(12) United States Patent
Ekinci

(10) Patent No.: US 10,444,623 B2
(45) Date of Patent: Oct. 15, 2019

(54) METHOD AND SYSTEM FOR HIGH-THROUGHPUT DEFECT INSPECTION USING THE CONTRAST IN THE REDUCED SPATIAL FREQUENCY DOMAIN

(71) Applicant: PAUL SCHERRER INSTITUT, Villigen Psi (CH)

(72) Inventor: Yasin Ekinci, Zurich (CH)

(73) Assignee: Paul Scherrer Institut, Villigen PSI (CH)

( * ) Notice: Subject to any disclaimer, the term of this patent is extended or adjusted under 35 U.S.C. 154(b) by 0 days.

(21) Appl. No.: 16/078,189

(22) PCT Filed: Feb. 2, 2017

(86) PCT No.: PCT/EP2017/052289
§ 371 (c)(1),
(2) Date: Aug. 21, 2018

(87) PCT Pub. No.: WO2017/144252
PCT Pub. Date: Aug. 31, 2017

(65) Prior Publication Data
US 2019/0056655 A1    Feb. 21, 2019

(30) Foreign Application Priority Data

Feb. 22, 2016  (EP) .................................. 16156736

(51) Int. Cl.
*G01N 21/00* (2006.01)
*G03F 1/84* (2012.01)
*G01N 21/956* (2006.01)

(52) U.S. Cl.
CPC ......... *G03F 1/84* (2013.01); *G01N 21/95607* (2013.01)

(58) Field of Classification Search
CPC ............. G01N 21/9501; G01N 21/956; G01N 21/95607; G01N 21/94; G01N 21/8806
(Continued)

(56) References Cited

U.S. PATENT DOCUMENTS

| | | | |
|---|---|---|---|
| 6,137,570 A | 10/2000 | Chuang et al. | |
| 7,570,800 B2 | 8/2009 | Lin et al. | |

(Continued)

FOREIGN PATENT DOCUMENTS

| | | |
|---|---|---|
| CN | 102171618 A | 8/2011 |
| JP | 2009520952 A | 5/2009 |

(Continued)

OTHER PUBLICATIONS

Tetsuo Harada, et al.: "Phase Defect Characterization on an Extreme-Ultraviolet Blank Mask Using Microcoherent Extreme-Ultraviolet Scatterometry Microscope". Journal of Vacuum Science & Technology B: Microelectronics and Nanometer Structures, vol. 31, No. 6, Jan. 1, 2013 (Jan. 1, 2013). p. 06F605, XP055318688, 2 Huntington Quadrangle, Melville, NY.

*Primary Examiner* — Md M Rahman
(74) *Attorney, Agent, or Firm* — Laurence Greenberg; Werner Stemer; Ralph Locher

(57) ABSTRACT

Methods and a system for scanning scattering contrast inspection for the identification of defects in an actual pattern block on a sample as compared to a desired pattern block. Most of the information in the reciprocal space (spatial frequency domain) is omitted in order to increase the throughput. That information in the reciprocal space is captured which gives the highest defect information, namely contrast signal between the defective and defect-free structure. Deviations from the expected diffraction pattern allow rapid identification of defects on the actual pattern. The first method learns the correct reconstructed diffraction image by comparing the repetitive pattern blocks. The second method (Continued)

focuses on the appearance of predictable defects in the spatial frequency domain of the reconstructed diffraction image thereby defining regions of interest where the defects materialize. Only the regions of interest are considered and compared to the reconstruction diffraction image of a defect-free pattern block.

17 Claims, 11 Drawing Sheets

(58) Field of Classification Search
USPC .................................................. 356/237.5
See application file for complete search history.

(56) References Cited

U.S. PATENT DOCUMENTS

| | | |
|---|---|---|
| 9,436,099 B2 | 9/2016 | Leewis et al. |
| 9,879,977 B2 | 1/2018 | Shchegrov |
| 2002/0187406 A1* | 12/2002 | Magome .................. G03F 1/78 430/5 |

FOREIGN PATENT DOCUMENTS

| | | | |
|---|---|---|---|
| TW | 201423080 A | 6/2014 |
| WO | 2014202341 A1 | 12/2014 |

* cited by examiner

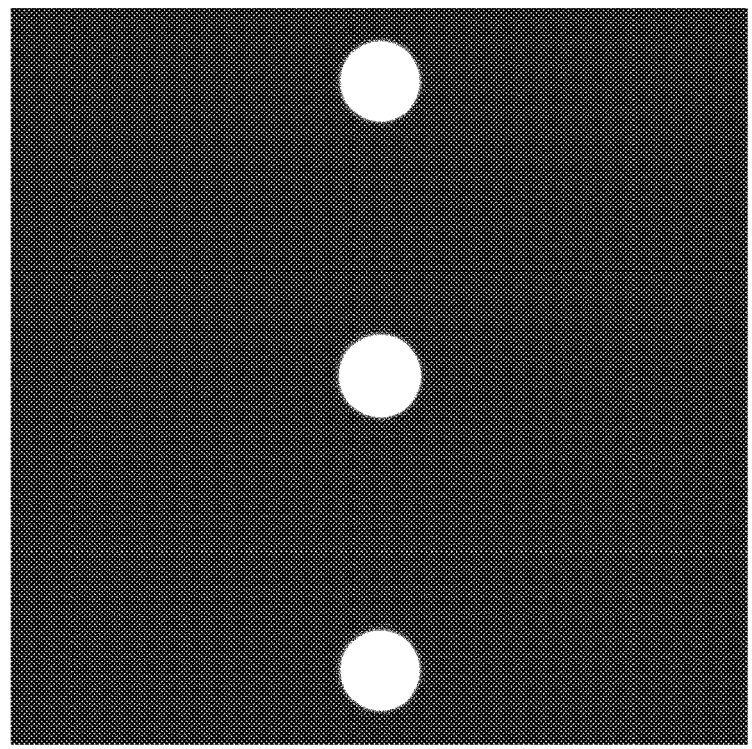
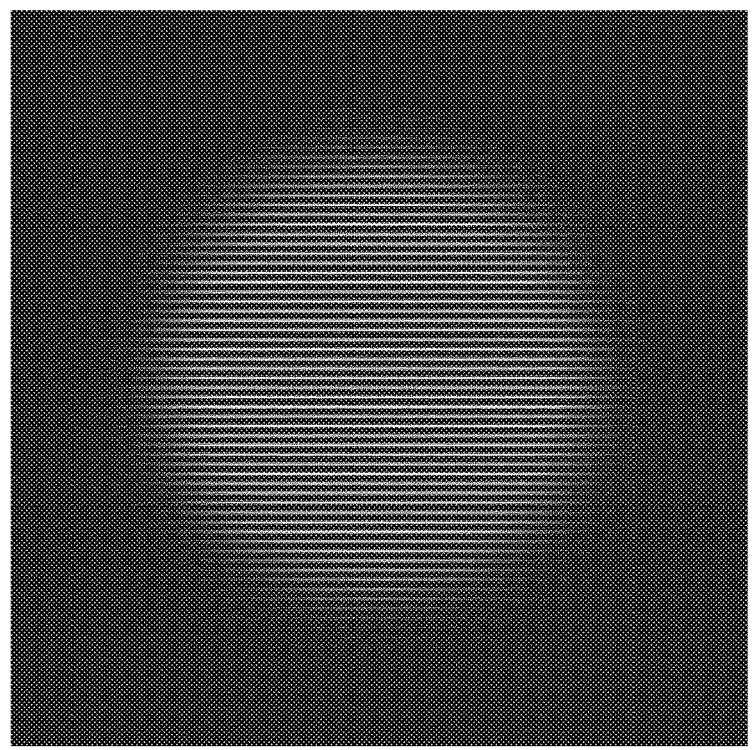
FIG 3
a)
b)

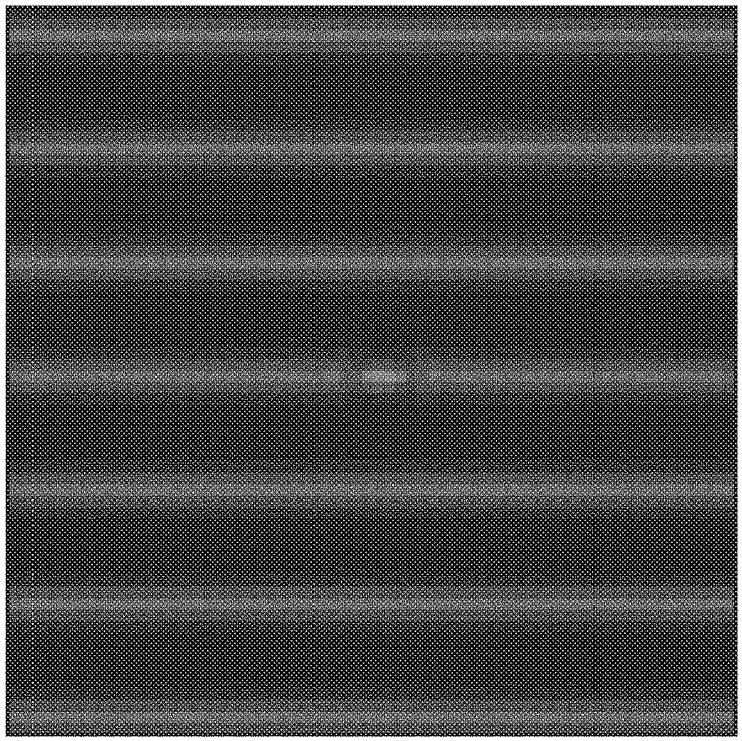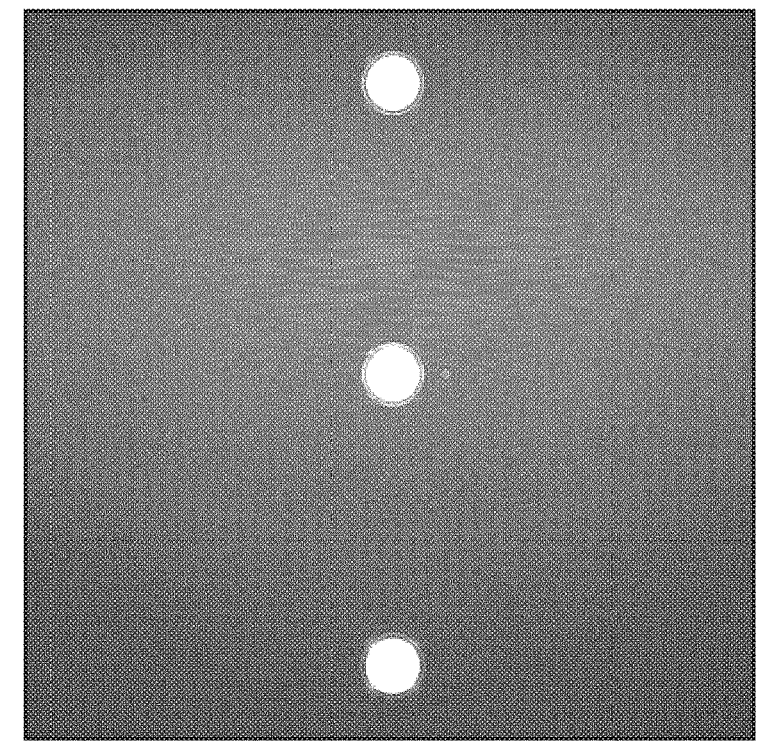
FIG 4
a)
b)

FIG 9
a)
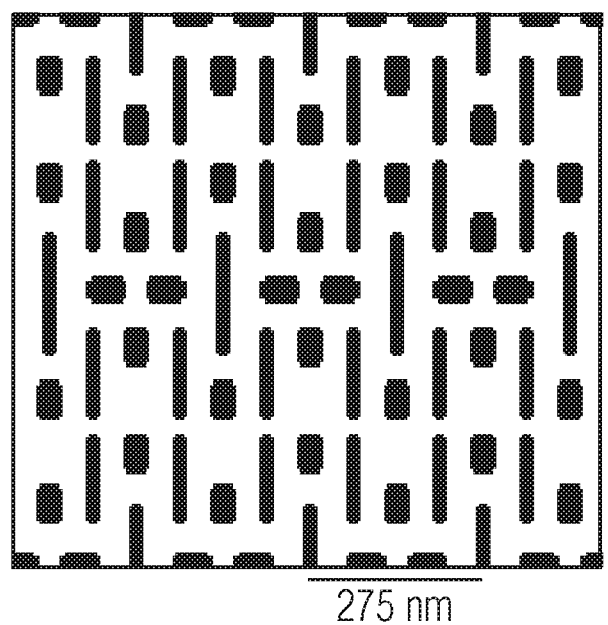
275 nm
b)
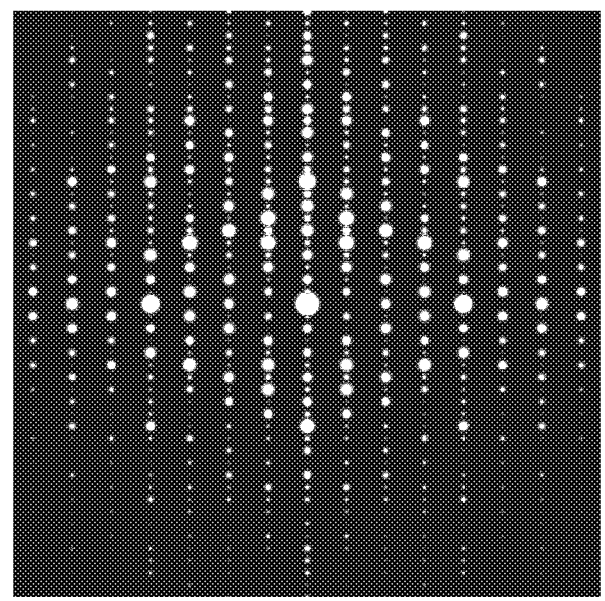

FIG 10
a) Mask layout
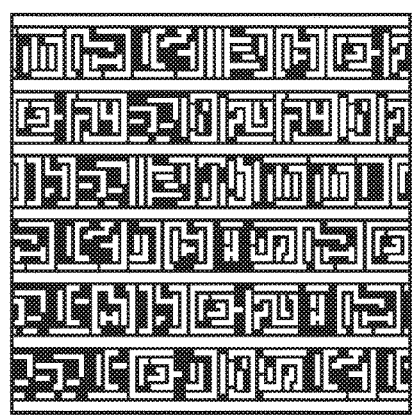
b) Diffraction pattern
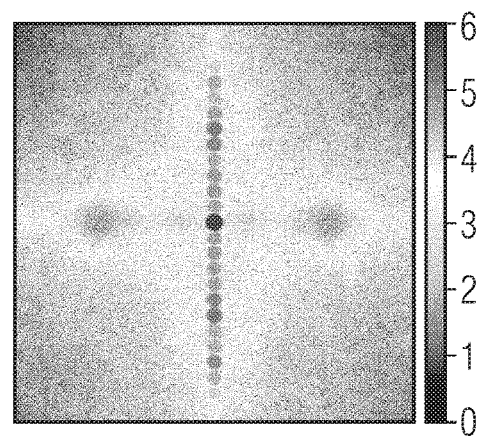
c) Layout with defect
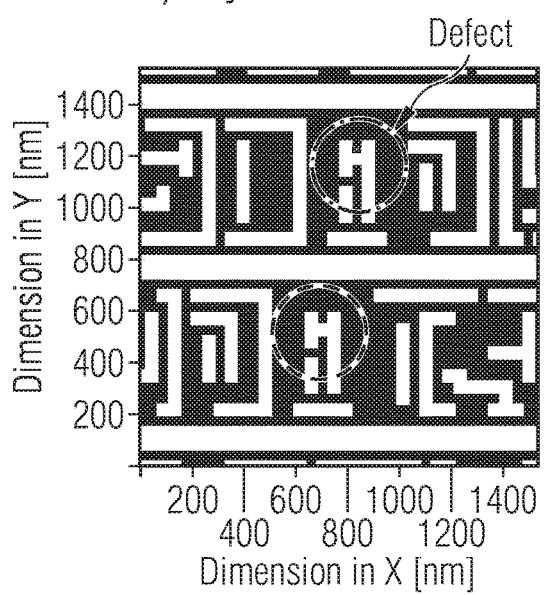
d) Near-field exit wavefront
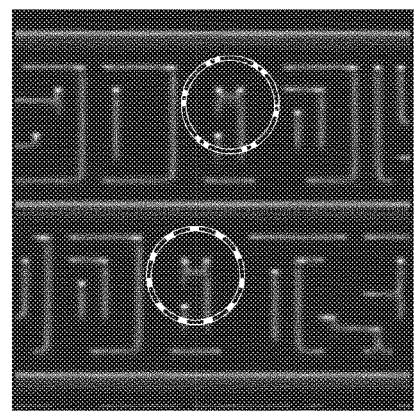

FIG 10
e) Contrast in diffraction pattern
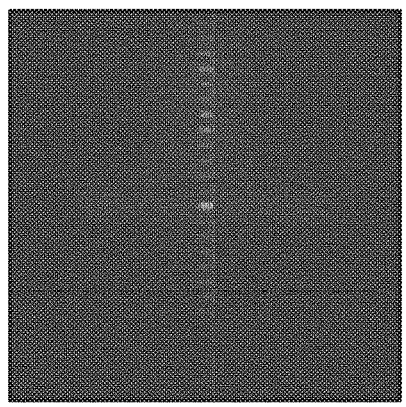
f) Contrast in diffraction patter nwith masks
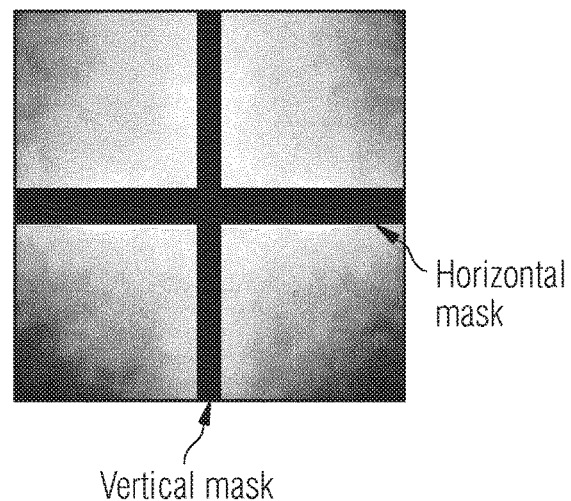
g) Comparison of signal and noise
|  | Total | In V mask | Out V mask | Out V & H masks |
|---|---|---|---|---|
| Signal | 3.18e6 | 0.94e6 | 2.24e6 | 1.72e6 |
| Noise | 7.43e4 | 6.07e+04 | 4.28e4 | 2.83e4 |
| SNR | 42 | 15 | 52 | 61 |

METHOD AND SYSTEM FOR HIGH-THROUGHPUT DEFECT INSPECTION USING THE CONTRAST IN THE REDUCED SPATIAL FREQUENCY DOMAIN

BACKGROUND OF THE INVENTION

Field of the Invention

The present invention relates to a method and a system using optical scanning and observation of scattered light for the identification of defects in an actual pattern block on a sample as compared to the desired pattern block on the sample.

Photolithography is a commonly used method for the production of micro and nanostructures used in integrated circuit technology and other commercial applications. Photolithography includes but not limited to DUV (193 nm), DUV immersion, EUV (13.5 nm), and X-rays. It is done using projection optics in which structures on a photomask are projected onto a wafer. Photomasks must be with low defect density, and ideally free of defects over several $cm^2$. Therefore photomask making involves multiple steps of inspection, review, and repair. The metrology methods and tools for sensitive and rapid identification and characterization of defects on mask blanks and patterned masks are therefore of great importance. Although different tools such as SEM and AFM are helpful, actinic metrology, i.e. optical inspection/review at the same wavelength and illumination conditions of a scanner is indispensable.

Particularly challenging is the actinic mask inspection of EUV lithography, which is the most promising route to face challenges of the semiconductor industry for high-volume manufacturing at the technology nodes below 22 nm half pitch. One of the major challenges of the EUV lithography is the provision of the masks with low defect density. Currently, there is a great and immediate need for such tools to detect and analyze phase and amplitude defects on mask blanks (multilayers) and patterned masks. The defects on the multilayer are mainly amplitude defects whereas the ones under the multilayer are purely phase defects. The defects within the multilayer lead to both undesired phase and amplitude modulation.

By inspection, metrology methods for mask review/inspection/characterization/evaluation of the masks are meant to be used for lithography. The aims include, but not limited to, obtaining the aereal image of the mask, identification of the defects and their characterization.

By mask blank, it is meant a transparent (a quartz plate for DUV) and reflective substrate (Bragg multilayer for EUV and soft X-rays). A patterned mask is, for example, the photomask after the designed patterns are written on the substrate using absorber or phase-shifting materials. The feature size of the patterns is, e.g., 4 or 5 times larger than the desired pattern on wafer. This means, for instance, for 11 nm half-pitch technology node the minimum feature size will be 44 nm.

The aims of inspection tasks may be different such as determination of defect density of mask blanks, identification of the defects (phase, amplitude, size, type of defect), comparison of defect density of blanks which went through different preparation or cleaning process, evaluation of a certain cleaning process if it is successful for removal of a previously identified defect, etc.

By actinic inspection, it is meant that the inspection is performed at wavelength and relevant incidence angle of the light. For EUV mask, this must be reflective and at incidence angle of 6 degrees at 13.5 nm wavelength. This is the standard condition for the use of the masks in real operation, i.e. lithographic production of semiconductor devices.

For an inspection tool, the following features or aspects are important:

1) Resolution is critical in order to resolve all the defects that contribute to the patterning in the lithographic process and thereby deteriorate the yield in fabrication process. On the other hand, for practical applications, it might be sufficient just to locate the defect, which may not require such a high resolution. For some purpose, even higher resolution might be necessary. For instance, to investigate the effects of line-edge roughness and tiny defects.
2) Sensitivity to the relevant defects, i.e. detection of the defects with high signal-to-noise.
3) Throughput is the most important parameter in practical applications. Since the mask sizes are relatively large (e.g. 100×100 $mm^2$), identification of defects with nanometer resolution is a great challenge. Since the detection is generally done with a pixel detector, such as CCD or CMOS detector, a detector-limited throughput should be achieved.

To exemplify the problem, wafer or photomask inspection using conventional methods can be considered. Regardless of scanning or full-field microscopy, the sample (photomask or wafer) is illuminated and the image is projected onto a pixel detector. For example, if a pixel resolution of 10 nm is targeted, this corresponds, for instance, a photomask of 100×100 $mm^2$ to $10^{14}$ pixels. To acquire this data within a reasonable time (e.g. $10^4$ seconds, i.e. less than 3 hours) a detector with a capability of 10 Gigapixel per second (Gpps) readout rate is needed, which will be a technical challenge in near future.

Therefore, optical inspection with conventional methods is becoming increasingly difficult in order to meet the requirements of resolution, sensitivity, and throughput simultaneously. Therefore, novel solutions are needed for future technology nodes.

SUMMARY OF THE INVENTION

It is therefore the objective of the present invention to provide a method and a system that allow to analyze the structure of the pattern of a sample for errors/defects using a rather simple set-up having a high throughput with high resolution and high sensitivity (signal-to-noise ratio).

With respect to the method, this objective is achieved according to the present invention by a method of scanning coherent scattering inspection (SCSI) for the identification of defects in an actual pattern block on a sample as compared to the desired pattern block on the sample, said method comprising the steps of:
a) providing the sample, either blank or having the actual pattern block, said pattern comprising absorbing and/or phase-shifting materials, wherein the sample comprises periodic repetitions of said pattern block;
b) providing a light source for generating a light beam for scanning the sample in transmission mode or reflection mode;
c) illuminating the sample with the light beam, preferably under an angle of 0 to 80°, thereby diffracting the light beam according to the actual pattern present on the sample;
d) detecting the diffracted light beam in terms of its position related intensities with a position sensitive detector;

e) analyzing the detected intensities, and thereby obtaining a diffraction image responsive to the actual pattern block on the sample;
f) repeatedly comparing the diffraction image with previously obtained diffraction image thereby determining a trustworthy diffraction image when a first predetermined number of diffraction images out of a second predetermined number of diffraction images are identically and marking all obtained diffraction images deviating from said trustworthy diffraction image as related to a pattern block potentially comprising a defect; and
g) identifying the position of the pattern block potentially comprising a defect for further inspection of this position on the sample.

An alternative solution for the method is provided according to the present invention by a method of scanning coherent scattering inspection for the identification of defects in an actual pattern block on a sample as compared to the desired pattern block on the sample, said method comprising the steps of:
a) providing the sample, either blank or having the actual pattern block, said pattern comprising absorbing and/or phase-shifting materials, wherein the sample comprises periodic repetitions of said pattern block;
b) providing a defect library comprising a number of possible defects that may occur for said pattern block and calculating diffraction images to be obtained at the detector for each possible defect thereby determining regions of interest in the diffraction image which deviate from a diffraction image for a defect-free desired pattern block;
c) providing a light source for generating a light beam for scanning the sample in transmission mode or reflection mode;
d) illuminating the sample with the light beam, preferably under an angle of 0 to 80°, thereby diffracting the light beam according to the actual pattern present on the sample;
e) detecting the diffracted light beam in terms of its position related intensities with a position sensitive detector;
f) analyzing the detected intensities, and thereby obtaining a diffraction image responsive to the actual pattern block on the sample and comparing the obtained diffraction image only in the predetermined regions of interest thereby identifying pattern blocks potentially comprising a defect; and
g) identifying the position of the pattern block potentially comprising a defect for further inspection of this position on the sample.

With respect to the system, this objective is achieved according to the present invention by a system for SSCI for the identification of defects in an actual pattern of a sample as compared to the desired pattern of the sample, said system comprising:
a) a sample holder for holding the sample being either blank or having the actual pattern, said pattern comprising absorbing and or phase-shifting materials,
b) a light source for generating a light beam for scanning the sample in transmission mode or reflection mode thereby illuminating the sample with the light beam, preferably under an angle of 0 to 80°;
c) a position sensitive detector for detecting the diffracted light beam in terms of its position related intensities;
d) means for data processing for analyzing the detected intensities in order to obtain a diffraction image of the actual pattern of the sample;
e) means for calculating a predicted diffraction image of the desired pattern, preferably using Fourier or Fresnel calculations;
f) means for comparing the measured diffraction contrast with measured or predicted diffraction pattern for the detection of an intensity variation deviating from the predicted diffraction image; and
g) means for identifying the position of the deviating intensity variation in order to produce a defect map for further inspection.

Therefore, the methods and the system here offer a novel solution in order to achieve defect sensitivity and throughput. This method omits the most of the information in reciprocal space (spatial frequency domain) in order to increase the throughput and it captures on the information in the reciprocal space that gives the highest defect information, i.e. contrast signal between the defected and defect-free structure. Subject of the present invention is that the investigation for only deviations from the expected diffraction pattern will allow rapid identification of the defects on the actual pattern of the sample. While the first method describes a method that learns the correct diffraction image, i.e. from defect-free sample, by the comparison of the repetitive pattern blocks, the second method focuses on the appearance of predictable defects in the spatial frequency domain of the reconstructed diffraction image thereby defining regions of interest where the defects materialize and speeds up the investigations since only those regions of interest have to be considered and compared to the diffraction image of a defect-free pattern block.

To the contrary, the conventional optical inspection systems collect all the information of the sample in the real space on the sample plane in pixelated format and identify the defects by comparing the images site-to-site or site-to-database. Firstly, the pixel size on the sample plane has to be sufficiently small in order to achieve resolution and sensitivity. In case of a detector read out speed becomes a bottleneck, there is a tradeoff between sensitivity/resolution and throughput. Second, conventional inspection systems require optics, which can be expensive, non-ideal (aberrations), and limited efficiency (limited light transmission) or not feasible. Moreover, imaging with optics has a limited depth-of-focus, which requires high-precision of stages and extremely flat samples which is difficult to obtain over very large distances of the sample. In addition, at the focus, optics-based imaging provides only the amplitude information of the sample and detection of phase structures and defects requires through-focus, i.e. 3D scan, in order to reconstruct the phase.

Compared to the imaging methods with optics, in the present inventive methods both amplitude defects and phase defects are extracted simultaneously with a 2D scan. Moreover, depth of focus is not critical compared to imaging with optics. Therefore, for structured samples (i.e. masks), a fast inspection can be executed on the comparison of the effective diffraction pattern of the sample and the diffraction pattern deducted from the desired pattern. Subject of the present invention is that the investigation for only deviations from the expected diffraction pattern will allow rapid identification of the defects on the actual pattern of the sample.

The present invention may have a broad range of applications since the light source may provide visible light or UV light, DUV light, EUV light, soft X-rays or hard X-rays depending on the spatial resolution to be achieved.

Typically, the actual pattern may be a structure of an electronic circuitry either a wafer for a semiconductor chip, such as photoresist patterns, an array of transistors, resistances, inductivities and/or capacitances or a photomask which incorporates phase and amplitude structures designed to provide the design of a specific layer of a semiconductor chip. This structure is engineered according to the needs and the desired functionality of the semiconductor chip, such as a processor or a mass storage device. Therefore, the desired pattern in this sense is identical to the engineered pattern of the sample.

The present method enables detecting the defects by analyzing the detected intensities by looking at their difference from the expected intensities. In order to determine the expected intensities at the detector, more precisely within the region of interest of the detector, rigorous calculations of light propagation and its interaction with the sample (including the patterns and substrate) are performed, which takes the illumination function on the sample, sample layout and its optical properties, optical configuration and detector specifications (pixel size and noise, etc.) into account and thereby precisely estimating what to be measured as intensity at every relevant pixel of the detector.

The contrast signal is the total sum of the differences at every pixel within ROI. Alternatively, the expected intensity is not needed to be estimated as described above but compared with the intensity profile measured at other sites. Typically the samples incorporate repetitive structures and most of the measured sites are defect-free and the defects are very rare and isolated. In this case, the aforementioned calculations can be skipped. The method can work in this set-up as self-learning. When the repetitive structures are scanned, the number of matches in the spatial domain can be used to define the trustworthy diffraction pattern. For example, in case that ten repetitive pattern block show the same diffraction pattern, this diffraction pattern is believed to the desired diffraction pattern. The number of repetitively matching diffraction pattern can be predetermined in order to determine the trustworthy diffraction pattern, i.e. something in the range from 5 to 50.

The region of interest (ROI) can be a single pixel and up to full frame of the detector depending on the pattern, desired sensitivity and targeted throughput. The region of interest is defined prior to experiment, depending on the patterns on the sample and potential defects. In semiconductor manufacturing the samples (wafers and photomasks) typically have relatively simple periodic or aperiodic structures, which are repetitive site-to-site, die-to-die and wafer-to-wafer. The types of defects are also to be well-known, since they occur due to stochastic processes or due to repeating but unavoidable errors in semiconductor manufacturing which is a highly routine process. The defects are isolated and have a certain shapes, locations and range of dimensions. Therefore, a defect library can be established for every sample and the optimal ROI is to be set according to the patterns and expected defects. ROI either set manually by intelligently judging the maximum contrast to be expected or it is set by an algorithm which runs through many possible combinations of defects and automatically judges for the best ROI for the targeted sensitivity and throughput.

The proposed method provides a 2D map of intensity contrast of the pattern block on the sample and by setting an intensity threshold it is converted to a binary defect map, which provides the location of the defects. The positions of the defects are determined within size of the illumination spot, which is relatively large. Typically, after a high-throughput generation of the defect map the accuracy of the position of the defect can be improved scanning the defect sites with a small spot size or multiple scanning with large overlaps. The defect sites can be reviewed, i.e. analyzed in detail, by other methods, such as, other optical imaging methods, scanning electron microscopy, or atomic force microscopy. In specific set-ups, the captured defects can be analyzed using lens-less imaging methods, i.e. coherent diffraction imaging methods, such as ptychographic algorithms, which reconstruct the aerial image of the sample from the scattered light profile at the detector. This is also a major advantage of the present system that allows also a detailed analysis of the defect with the same setup. After obtaining the defect map, the defect sites can be analyzed in detail with the same setup, which is also suitable for coherent diffraction imaging methods. In this case the defect sites are imaged by obtaining the full frame scattering information and in a slow manner.

BRIEF DESCRIPTION OF THE SEVERAL VIEWS OF THE DRAWING

The present invention and its preferred embodiment are hereinafter described in more detail with reference to the attached drawings which depict in:

FIG. 3 schematically an aerial image of a perfect line pattern (a) and its respective obtained diffraction image (b);

FIG. 4 schematically an aerial image of a line pattern having a 20 nm π/4 phase defect (a) and its respective diffraction image (b);

FIG. 9 schematically a pattern block being representative for an SDRAM cell (a) and its respective diffraction image (b);

FIG. 10 schematically a pattern block being aperiodic and reprensentative for a logic cell.

DESCRIPTION OF THE INVENTION

Figure 1:
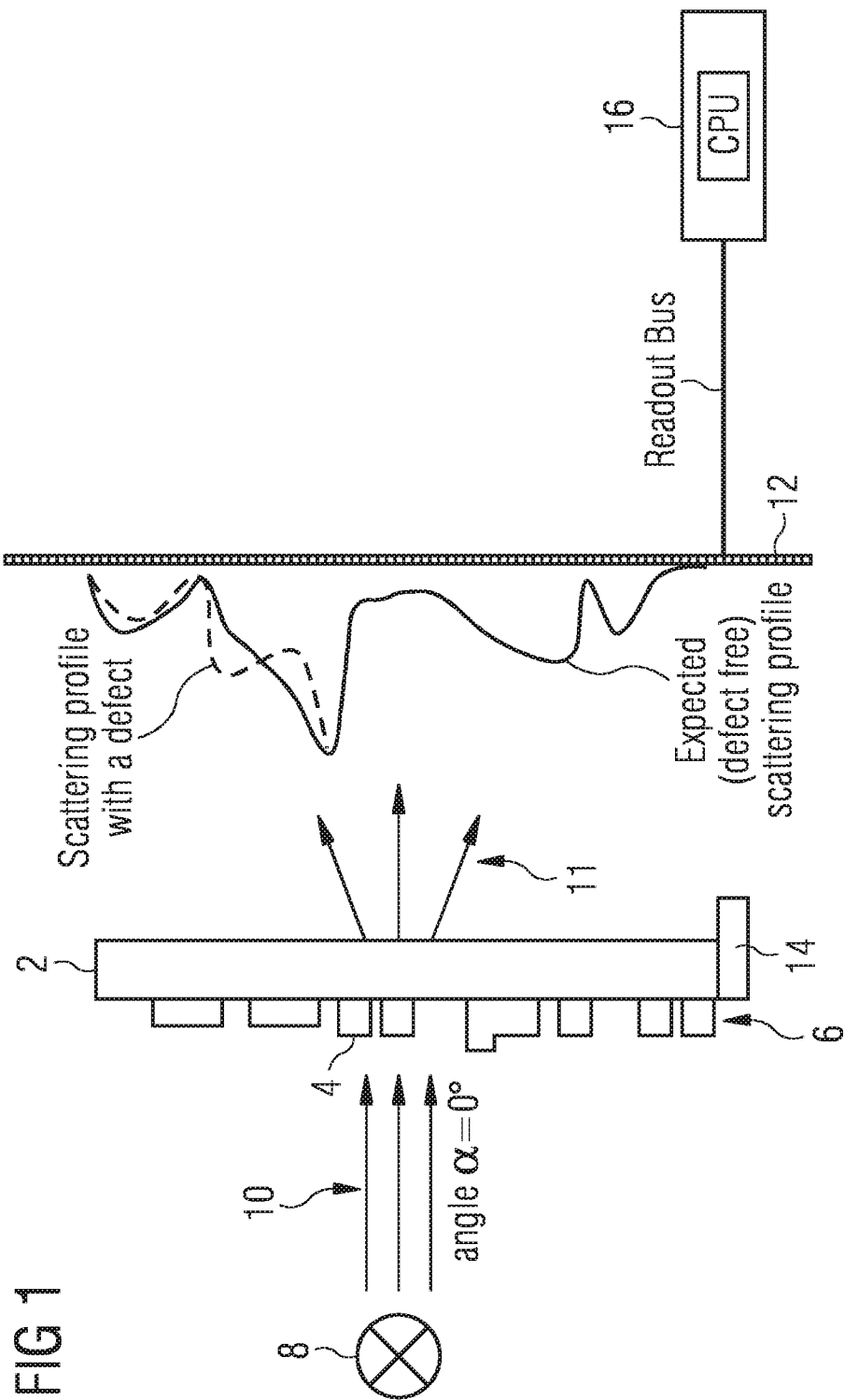
FIG. 1 schematically the method of the inspection of a patterned sample according to the differential coherent scattering technique in transmission mode.

FIG. 1 schematically illustrates the concept of the present invention involving a method and a system of analyzing or inspecting samples 2 for defects 4 in transmission mode. In many cases, including but not limited to, the major interest is locating the defects 4 and their characterization. A defect 4 is a void or particle perturbing an intended (desired) pattern block 6 or size or thickness variation from the desired pattern or on a flat surface of a blank sample. A fast inspection of the samples 2 with high sensitivity is needed. In the example according to FIG. 1, the pattern block 6 is comprises an ensemble of absorbing or phase shifting artefacts disposed on the surface of the sample 2. On semiconductor sample, such as a wafer, this pattern block can be a layer of a semiconductor device or its corresponding photoresist pattern, which usually is repetitively disposed on the sample 2. Therefore, a sample 2 may comprise a structure of lines and columns of these pattern block 6 which can be repeated several hundred or thousand times per line and/or column.

One of artefacts is designated as a defect 4 because this artefact is not projected in the desired pattern block but is erroneously present in the actual pattern block 6. The artefacts and its arrangement correspond, for example, to a final illumination pattern of a wafer surface that can be made subject to an etching step or the like in CMOS wafer production in semiconductor industry.

Therefore, the pattern block 6 is usually internally irregular (no periodicity within the pattern block 6). In wafer production, the mask used for the illumination of the wafer may comprise this pattern block 6 repeatedly disposed over the mask surface which yields to a periodicity of the pattern block 6 (the pattern block 6 is repeated at an integer number of times over the surface of the wafer mask).

The proposed method is a technique in which a diffraction profile is recorded with a position sensitive detector, such as a pixel detector 12 (also called pixelated detector 12). The terms "diffraction" and "scattering" are synonymously used in this text. The sample 2 is either blank or patterned with absorbing or phase-shifting materials (see the pattern block 6 on the surface of the sample 2). It has to be mentioned here that the pattern block 6 might have a certain periodicity wherein the pattern block 6 itself is usually heterogeneously (irregular), i.e. the pattern block of an individual storage cell. This may for example apply to a certain structure in CMOS technology (i.e. an array of transistors) that is numerously repeated on the surface of the sample 2 used as a mask for wafer production. In this case, the pattern block 6 is internally nonperiodic, but the whole pattern block 6 is repeated numerously on the surface of the wafer mask.

Figure 2:
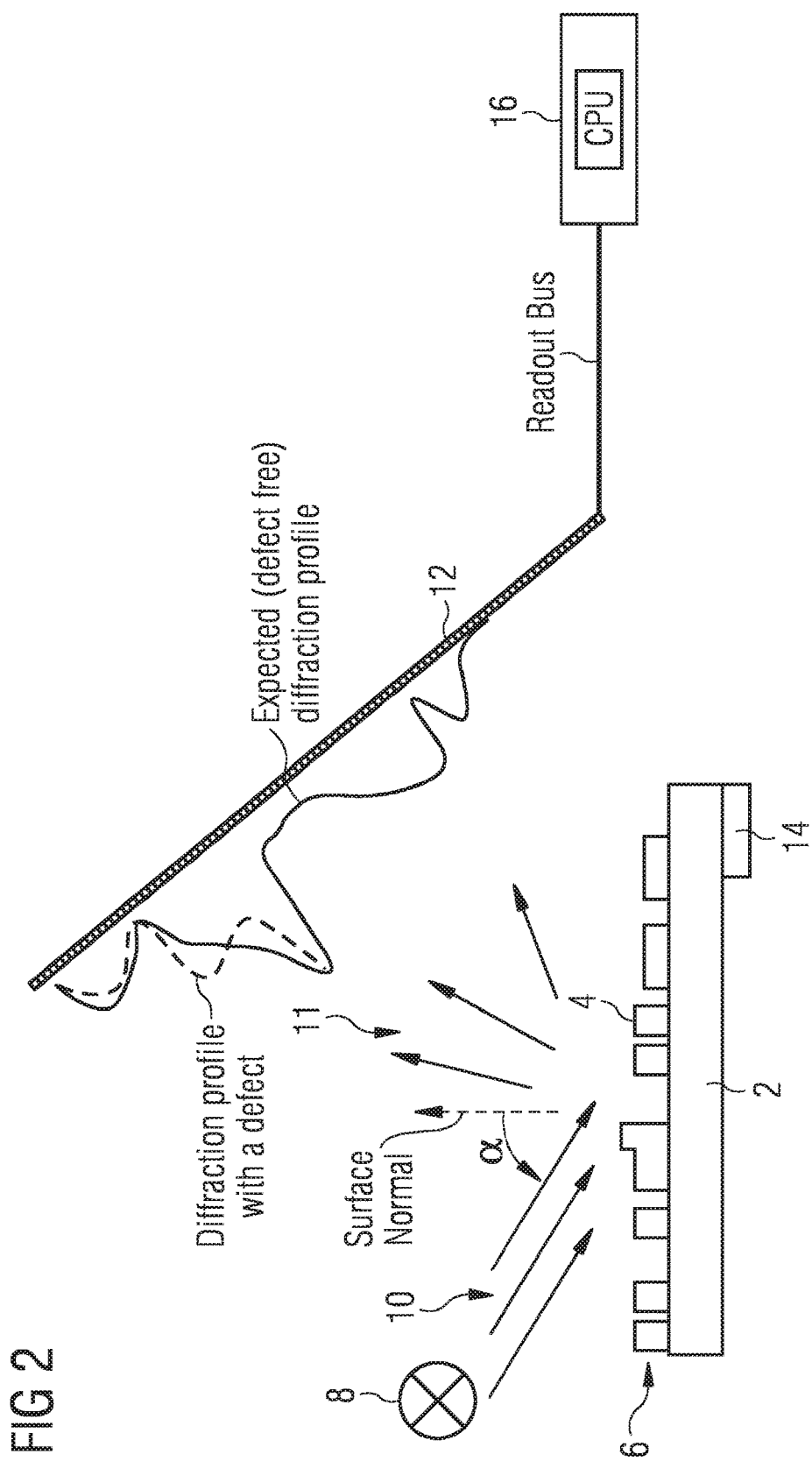
FIG. 2 schematically the method of the inspection of a patterned sample according to the differential coherent scattering technique in reflection mode.

Due to disadvantageous circumstances during sample production, the desired or engineered pattern block may not be identically transferred to the sample, i.e. a wafer mask, (some areas comprise correct copies of the desired pattern, others may comprise patterns blocks with defects, such as the pattern block 6 shown with the defect 4 in FIGS. 1 and 2) resulting therefore in a faulty wafer production. Since the desired pattern block is known and the diffraction image of this desired pattern block can be calculated, for example by using Fourier or Fresnel algorithms, the images of the detected diffraction light intensities can be compared to the calculated diffraction image of the desired pattern block. When this comparison yields a deviation (image mismatch as shown in FIGS. 1 and 2 as deviation of the dashed line from the solid line) indicative for a defect in the pattern block 6 of the sample 2, a candidate region, i.e. a defect site, for further sample inspection has been identified. This situation is represented in FIGS. 1 and 2 where the intensity distribution of the detected image (dashed line) does not match the expected intensity distribution (solid line) due to the undesired artefact (defect 4) causing a deviating intensity distribution.

In FIG. 1, the light source is an X-ray source 8 (such as from a synchroton source or a high-harmonic generation) illuminating the surface of the sample 2 being supported by a sample holder 14 with a coherent light beam 10. The light source in this example is an X-ray source. In other setups, the light source could be a source for emitting visible light or UV or DUV or EUV or soft or hard X-rays. The diffracted beam 11 responsive to the pattern block 6 disposed on the sample 2 in this example is recorded in transmission mode by the pixel detector 12 (the setup in FIG. 2 show coherent diffraction imaging in reflection mode). Since the pattern block 6 on the sample 2 is known a priori or since it is known that there should be no pattern in case of a blank sample and the respective diffraction profiles are predicted at the detector plane using Fourier or Fresnel calculations. The detected diffraction profile is compared with the predicted diffraction profile. If the profiles do not match, this indicates a defect, and thus its position is located. This evaluation is done in a data processing unit 16 which is connected via a readout bus to the pixelated detector 12.

In order to improve the speed and throughput of the error detection method, the present invention provides some particular method steps for scanning coherent scattering inspection for the identification of the defects 4 in the actual pattern block 6 on the sample 2 as compared to the desired pattern block on the sample 2.

First, the sample 2 is provided, either blank or having the actual pattern block 6, said pattern block 6 comprising absorbing and/or phase-shifting materials, wherein the sample 2 comprises periodic repetitions of said pattern block 6.

A further step provides a defect library comprising a number of possible defects that may occur for said pattern block 6. For each of these possible defects diffraction image is calculated thereby determining regions of interest in the reconstructed diffraction image which deviate from a reconstructed diffraction image for a defect-free desired pattern block 6. In particular, these deviations are representative for the respective defect. Therefore, the analysis of the reconstructed diffraction images can be limited to these specific regions of interest. These regions of interest can correspond to just a low number of detector pixels as well as to a specific larger region of detector pixels. Simple examples for those defects and their respective manifestations in the spatial domain are discussed in more detail below.

Within the method, the light source 8 has to be provided for generating the light beam 10 for scanning the sample 2 in transmission mode (FIG. 1) or reflection mode (FIG. 2). During the investigation, the sample 2 is illuminated with the light beam 10, preferably under an angle of 0 to 80°, thereby diffracting the light beam 10 according to the actual pattern block 6 present on the sample 2. The diffracted light beam 11 is detected in terms of its position related intensities with the position sensitive detector 12. The detected intensities are analyzed, and thereby obtaining a diffraction image responsive to the actual pattern block 6 on the sample 2.

According to an essential step of the present method, the obtained diffraction image is only compared in the predetermined regions of interest thereby identifying pattern blocks 6 potentially comprising a defect 4. If the region of interest show a noticeable content, the position of the pattern block 6 potentially comprising a defect 4 is identified for further inspection of this position on the sample 2.

Preferably, once the defect 4 is located, it can be characterized in detail by using coherent scattering microscopy (CSM) algorithms with the already collected data or with subsequently collecting more detailed data of diffraction profile. We call this method as scanning coherent scattering contrast inspection (SCSCI) which is a lens-less, high-resolution inspection using sample scanning and collecting the scattering/diffraction images and enables identification and location of defects 4 on samples 2. Subject of the present invention is that the investigation for only deviations in the region of interest from the normal expected diffraction image will allow rapid identification of the defects 4 on patterns 6 blocks that are known or predicted a priori. One advantage of this method is that it is faster than other imaging methods, in the case that inspection speed is limited by the detector read out speed. In many cases, the pattern blocks 6 are well-known and periodic (in short range or long range) as well as there are mostly certain types of defects expected on the sample 2. The detector read out area can be limited to the regions of interest where the scattering profile has the highest sensitivity to the defects 4.

Another method according to the present invention can apply a rather self-learning approach when identifying possible defects. Since the pattern blocks are disposed repeatedly on the sample, only a very few number of pattern blocks will comprise a defect. For that reason, the method may involve the same experimental setup and the same illumination steps, but the evaluation of the data is handled in a different self-learning way. This approach does not necessarily require to know the desired interference pattern in advance. During the investigation, pattern block(s) are illuminated one after the other(s). Since the major part of the pattern blocks are defect-free, the diffraction images will look the same for defect-free pattern blocks. The more the detected intensities are analyzed, and thereby diffraction image (s) responsive to the actual pattern block (6) on the sample (2) are achieved, the more a trustworthy diffraction image indicative for a defect-free pattern block can be identified.

In detail, by repeatedly comparing the obtained diffraction images with previously obtained diffraction images a trustworthy diffraction image is learned and can be identified when a first predetermined number of diffraction images out of a second predetermined number of diffraction images are identically. Only those diffraction images deviating from said trustworthy diffraction image are in the following marked as being related to a pattern block potentially comprising a defect. As a simple example, a detection of 10-times the same diffraction image out of a group taken for 11 pattern blocks indicates that the diffraction image being 10-times identical can be determined as the trustworthy diffraction image. Consequentially, only one out of the 11 pattern block deviated diffraction image-wise from the trustworthy diffraction image being therefore marked as a pattern block potentially comprising a defect. In the following, the position of the pattern block potentially comprising a defect is identified for further inspection of this position on the sample 2.

Moreover, the self-learning method maybe included into the determination of ROI. Since the similar defects are recurring and the samples that are manufactured in the same way incorporates same type of defects due to the manufacturing steps, this accumulated knowledge can be used to optimize the ROI (for the highest speed and sensitivity) using algorithms. After measuring many diffraction image from many defect sites, the diffraction images can be used for further optimization of the RIO.

For the detailed analysis of the defect sites, i.e. review, lensless imaging techniques such as ptychographic algorithms can be used in order to obtain the exact location and the geometry of the defect or defects within the defect site. For this purpose, the defect sites should be scanned using the same setup but with a slow scan, i.e. full frame diffraction data and more overlap of the illumination so that the diffraction data is sufficiently redundant to reconstruct the aerial image of the sample.

The present invention combines the advantages of lensless imaging methods which have the advantages of resolution (which is not limited with optics), being a lensless method (e.g. high NA EUV optics is very expensive, making high-resolution inspection tools costly), large depth of focus, and the ability to obtain both amplitude and phase information with 2D scan. The latter advantage is particularly important for EUV masks, because the phase defects are difficult to obtain. Phase information can be obtained using optics and through-focus scans. This however reduces the throughput of the imaging, which is very important for EUV mask metrology.

Moreover, the a priori knowledge of the sample can be used in the reconstruction algorithms. The predicted aerial image of the sample can be used as an initial guess of the iterative reconstruction process, facilitating a fast convergence of the iterations. In addition, the predicted aerial image can be used to impose strong constraints on the reconstructed image, enabling reconstruction with less redundance of the data.

The present invention proposes two novel methods of differential CDI. Subject of the present invention is the inspection of sample, which are a priori known and the investigation for only deviation from the expected diffraction pattern will allow rapid identification of the defects on some areas. After the identification of the defects, these areas of interest can be analyzed in detail and the image can be reconstructed using methods such as ptychograhy.

FIG. 2 shows the corresponding configuration for reflective imaging using scanning CDI. In this example, the light beam 10 illuminates the surface of the sample 2 under an angle $\alpha$. Typically in EUV applications is an angle of 6°. This angle $\alpha$ can be different in other applications according to the specific needs and set-ups.

It is noted that in all the figures, CCD refers to any type of pixelated detector and not limited to soft X-ray CCDs.

Further, it is noted that the methods and setups disclosed in this invention are also valid at other wavelengths such as UV, DUV, BEUV and soft X-rays. For structured samples, such as masks for wafer production, with a periodicity of an heterogeneous pattern 6, a fast inspection can be executed by steps of multiples of period, which should give the same diffraction image responsive to the repeatedly disposed pattern 6. Subject of the present invention is that the investigation for only deviation from the normal diffraction image responsive to the pattern 6 will allow rapid identification of the defects on periodic mask patterns. Compared to other CDI methods, a priori knowledge of the illumination is not needed. Both amplitude and phase are extracted whereas optics-based imaging requires through-focus imaging in order to reconstruct the phase.

FIG. 3 now shows schematically an aerial image of a perfect line pattern (a) and its respective reconstructed diffraction image (b). The lines have distance of 20 nm. The respective reconstructed diffraction images show three rather sharp circles of intensity response.

FIG. 4 now schematically depicts an aerial image of a line pattern having a 20 nm $\pi/4$ phase defect (a) and its respective diffraction image on the detector plane. The three rather sharp circles of intensity response are still present but apart from that some artefacts appear, i.e. small circle below the circle in the middle of the image.

Figure 5:
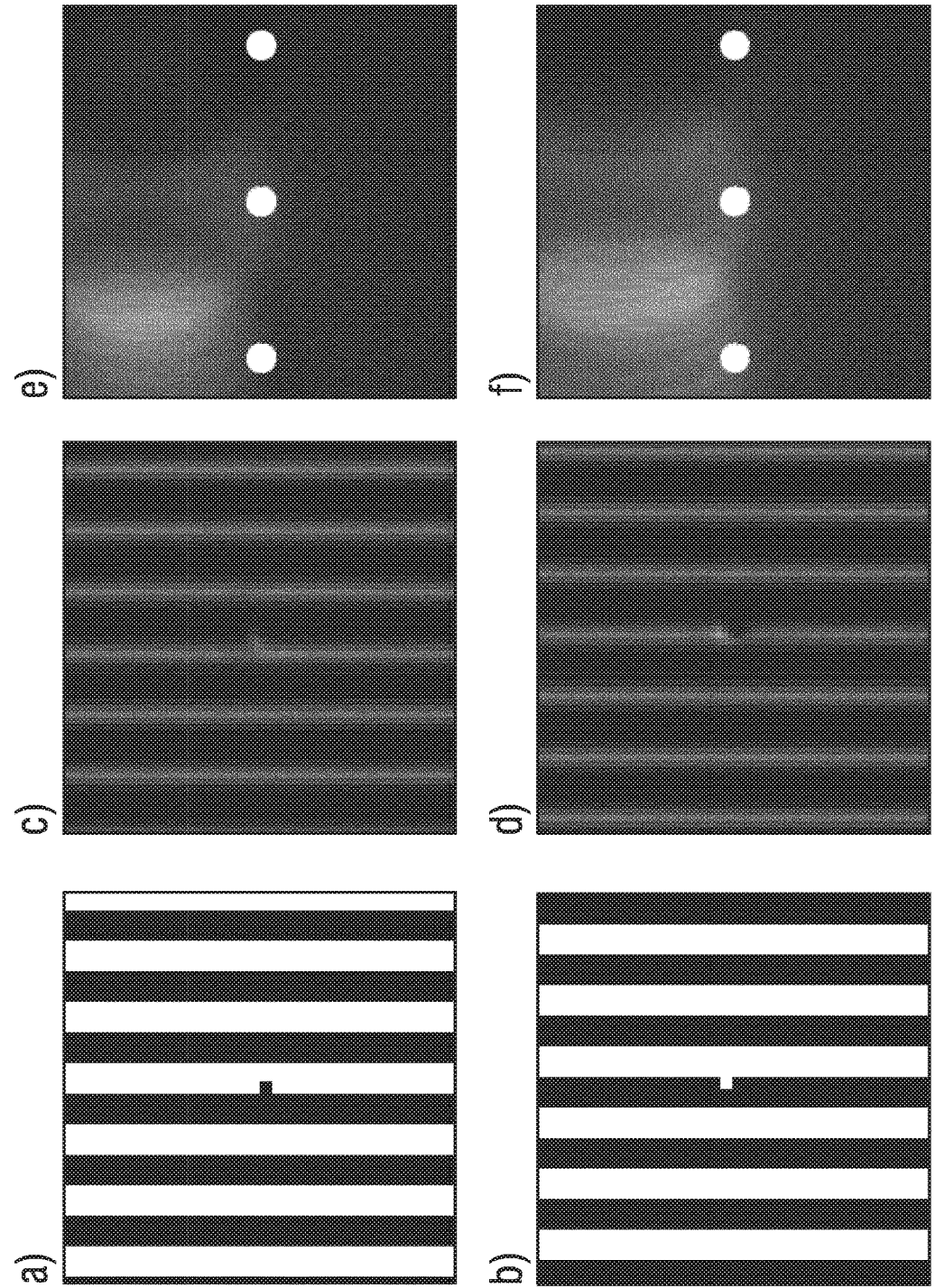
FIG. 5 schematically a mask pattern having a line pattern with an extrusion defect (a) and the same mask pattern with an intrusion defect (b) and the respective aerial images (c) and (d) resp. as well as the respective diffraction images (e) and (f) resp.

Similar responses are represented in FIG. 5 which schematically depicts a mask pattern having a line pattern with an extrusion defect (a) and the same line pattern with an intrusion defect (b) and the respective aerial images (c) and (d) resp. as well as the respective diffraction images (e) and (f) resp. Also these defects cause specific artefacts apart from the image shown in FIG. 3(b) for a defect-free line pattern.

Figure 6:
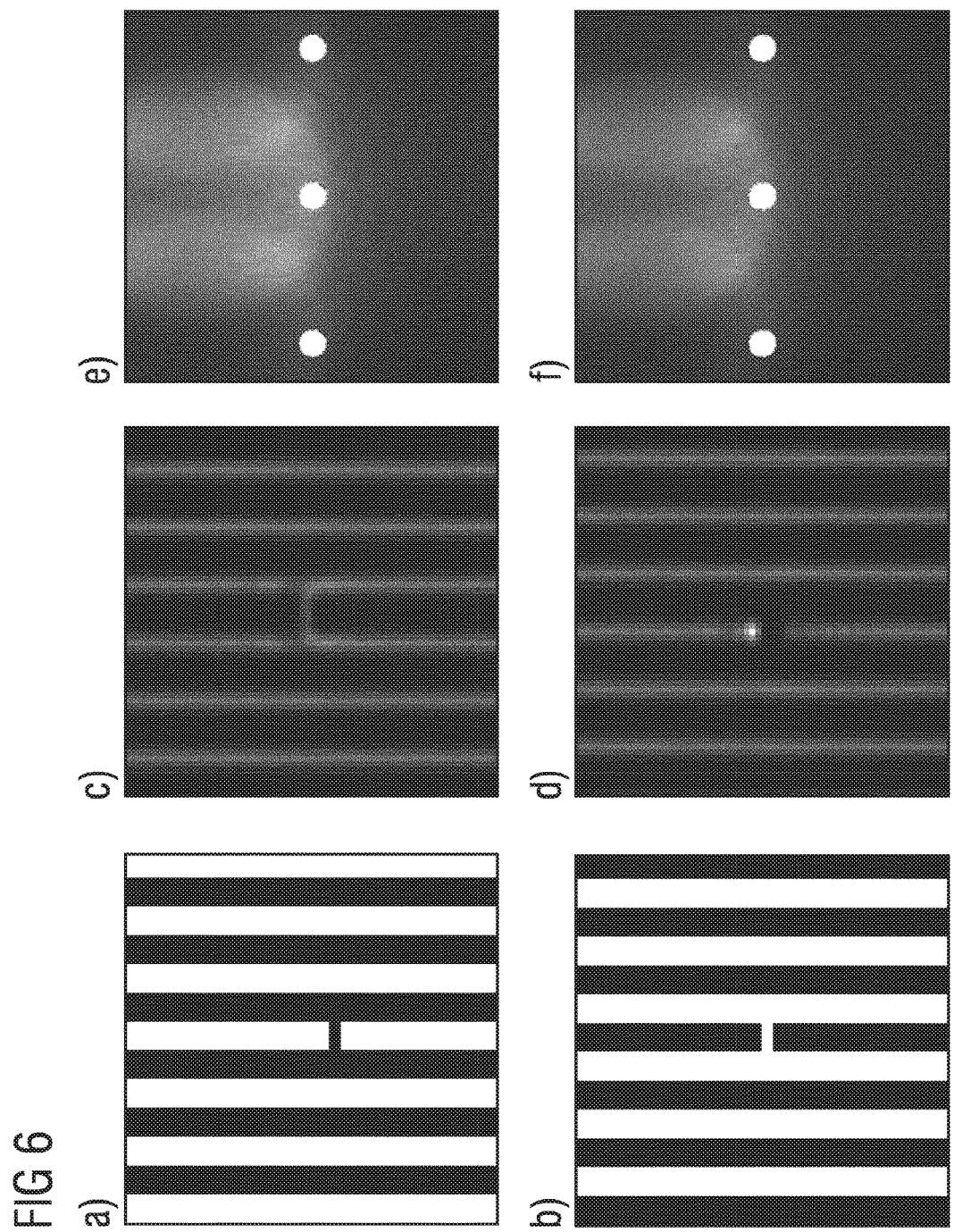
FIG. 6 schematically a mask pattern having a line pattern with an bridge defect (a) and the same mask pattern with an gap defect (b) and the respective aerial images (c) and (d) resp. as well as the respective diffraction images (e) and (f) resp.

Further, also FIG. 6 schematically represents a mask pattern having a line pattern with an bridge defect (a) and the same mask pattern with an gap defect (b) and the respective aerial images (c) and (d) resp. as well as the respective diffraction images (e) and (f) resp. Again, the responsive artefacts occur as compared to the ideal image in FIG. 3(b).

These defect types can be now collected within the defect library. As regions of interest, in particular the area with the occurrence of the artefacts apart from the ideal image representing the ideal defect-free line pattern needs to be investigated.

Figure 7:
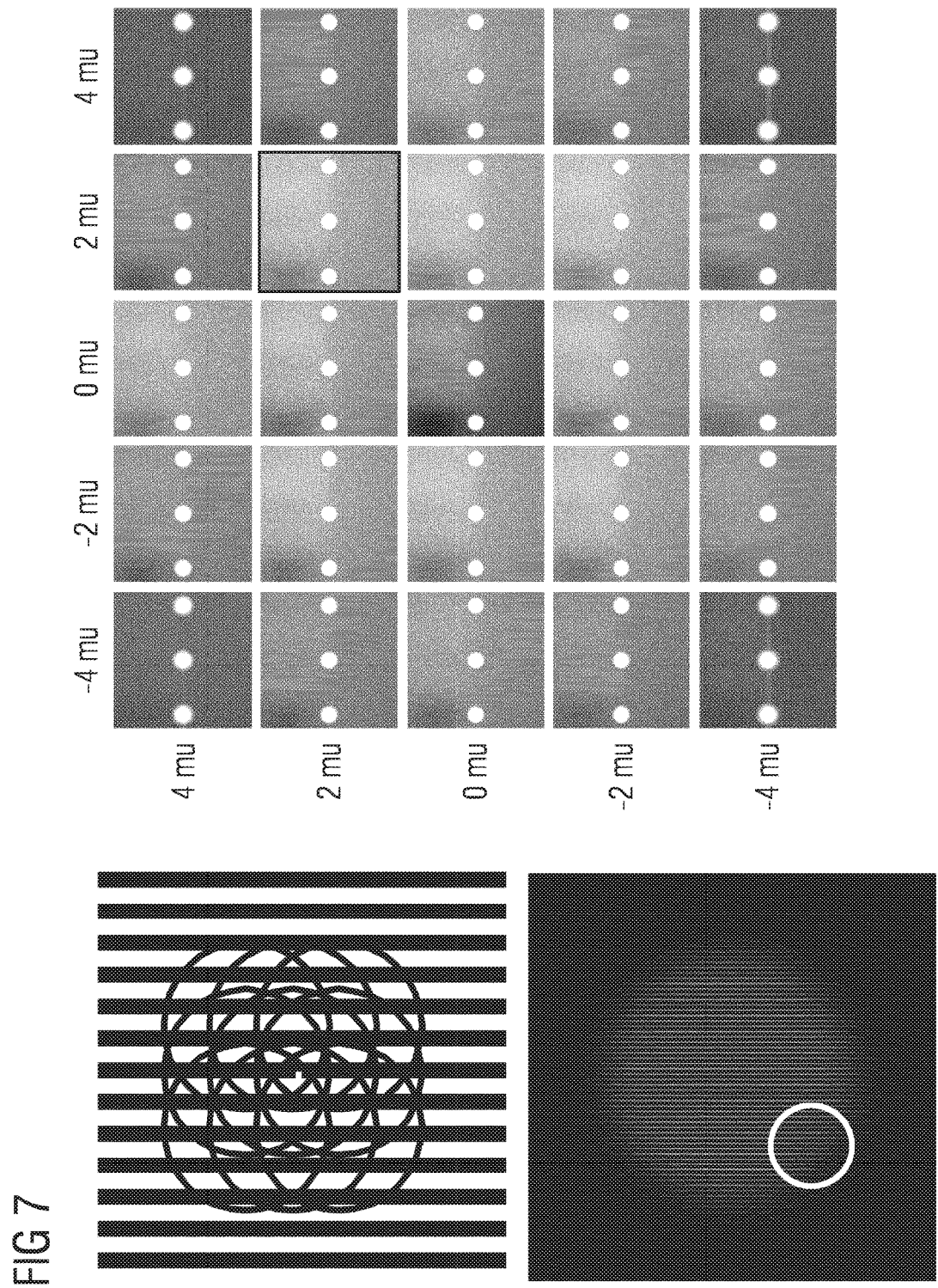
FIG. 7 schematically the process for the defect mapping of an indentation comprised in a mask pattern having a line pattern.

FIG. 7 schematically the process for the defect mapping of an indentation comprised in a mask pattern having a line pattern. During the scanning and collection of diffraction images, the sample is illuminated with a relatively large spot size. FIG. 7a shows the grating sample and the illumination area for a single defect in which the defect is close to the edge. FIG. 7b show various cases where the illumination spot position is different for a single defect. FIG. 7c shows the diffraction images for various cases where the position of the defect relative to the center of the illumination spot is changed in 2 micron steps for both horizontal and vertical axes. In all cases a reasonable diffraction image indicating the defect is obtained.

Figure 8:
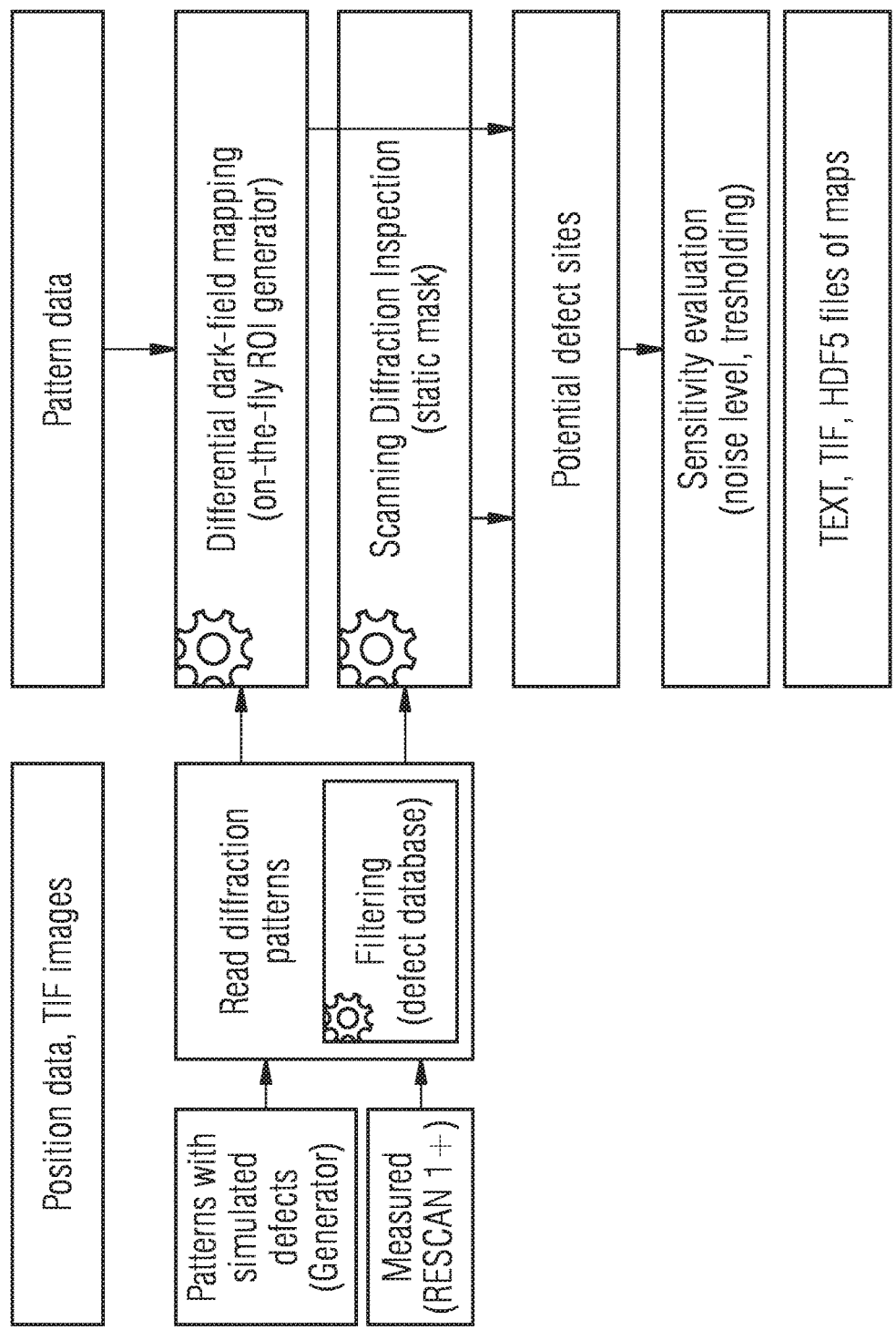
FIG. 8 schematically a diagram of the functionality of a defect inspector.

FIG. 8 shows the schematics of the algorithms for the defect inspection. This flowchart provides an example for die-to-die and die-to-database comparisons of diffraction images to create a defect map.

The examples above show the principle of the method for a 1D periodic pattern. The same principles are valid for a 2D periodic pattern or more complex periodic and nonperiodic patterns.

FIG. 9 schematically a pattern block being representative for an SDRAM cell (a) and its respective diffraction image (b). The diffraction image shows the spatial frequencies of this complex pattern of the sample. is reconstructed diffraction image could be now subject to the self-learning approach mentioned above. After repetition of a number of for example 10 identical diffraction images, the reconstructed diffraction image is determined as trustworthy reconstructed diffraction image and further reconstructed diffraction images are evaluated against this trustworthy diffraction image. Starting from this trustworthy diffraction image, the methods could be also combined. As region of interest, the area without the highlighted spots (outside the diffraction peaks) can be defined. Therefore, the desired diffraction image can be learned for rather complicated pattern blocks as the one shown in FIG. 9(a) and the region of interest can be derived from this learned trustworthy diffraction image.

Alternatively, the diffraction pattern of the sample can be predicted and region of interest can be defined with respect to the predicted diffraction image of the sample and its deviation from the ideal diffraction image due possible defects, which are listed in the defect library.

FIG. 10 shows a typical mask layout (a) for a logic device. In this example the periodic thick horizontal lines represent power rails whereas the fine features are completely aperiodic. FIG. 10(b) shows the diffraction pattern from such a mask. Distinct and sharp diffraction peaks are due to the periodic lines of the pattern whereas the aperiodic pattern leads to a diffused diffraction pattern. FIG. 10(c) shows a case in which a programmed defect is introduced into the design. The defect, in this case, is a thicker line than it is intended, which represents a typical defect in a photomask. The defect modifies the aerial image of the mask which is shown in FIG. 10(d). The effect of the defect on the aerial image is small but discernable. In a typical diffraction/scattering contrast microscopy two approaches exist to identify the defects. In die-to-die inspection diffraction patterns are compared, i.e. substracted at the pixel level and integrated for all pixels. If this contrast signal is above a certain threshold a defect is identified. The threshold is above the noise level which is defined by the detector noise, diffuse scattering from the sample due to roughness, detector and source fluctuations, etc. In die-to-database inspection, in the first step, the aerial image of the mask is calculated by using all the necessary input data, including but not limited to, the mask layout and structural parameters and material properties of the mask, and illumination conditions. In the next step, the aerial image is propagated to the detector plane using Fourier transforms and hence the predicted diffraction pattern of a defect-free mask can be calculated. The constrast signal in this case is the difference between calculated and measured diffraction patterns. Such a difference for the mask layout (in FIG. 10(a)) and the considered defect (in FIG. 10(c)) is shown in FIG. 10(e). Most of the contrast signal is within the diffraction peaks due to the periodic features of the masks, since these peaks are highly intense. The constrast signal, noise, and signal-to-noise (SNR) ratios from this defect are listed in FIG. 10(g). The first column refers to the values obtained by reading the whole detector. Although most of the defect signal is on the vertical and central part of the detector, the SNR value is reduced by the noise which is mainly due to the shot noise of intense diffraction peaks along the vertical axis at the center as can be seen in FIG. 10(b). If one takes a vertical mask area as shown in FIG. 10(f) and only consider the contrast signal within this area, the SNR value of the defect decreases as listed in the second column of FIG. 10(g). If the defect signal outside the vertical mask area the SNR value of the defect significantly increases (third column in FIG. 10(g)). Further enhancement of SNR can be achieved by blocking the central area along the horizontal axis because this is also an intense area of the diffraction pattern of a defect-free mask.

The masked areas can be increased further, i.e. the area of detection can be reduced until an optimal SNR value is reached. The optimal areas to be read out or to be analyzed are not discussed here. The example is given to illustrate the feasibility of detection of a defect on an aperiodic pattern and at frequency domain and improvement of signal to noise ratio by reducing the detection area. The optimal detection area depends on the patterns, type of potential defects and experimental parameters, i.e. detector, illumination, etc. Whereas there is an optimal detection area for the maximum SNR for the defects, the throughput, i.e. the speed of inspection, will increase with reducing the detection area for the inspection experiment which is limited by the speed of detector readout. In reducing the detection area in the frequency domain, both the speed and SNR increase by reducing the detection area until the optimal detection area is reached.

Therefore, the optimization of the detection area provides double advantage, i.e. increased SNR and increased speed. Further reduction of the detection area leads to increased speed and reduced SNR.

The optimization of the detection area depends on many factors, including the patterns to be inspected, type of possible defects, and instrumental parameters. A possible approach would be carrying out extensive simulations or experiments on programmed defects for a given pattern and a list/library of potential defects. Another approach is to use machine learning.

The invention claimed is:

1. A method for scanning scattering contrast inspection for the identification of defects in an actual pattern block on a sample as compared to a desired pattern block on the sample, the method comprising the steps of:
   a) providing the sample with the actual pattern block, the pattern including absorbing and/or phase-shifting materials, and the sample having repetitions of said pattern block;
   b) providing a light source for generating a light beam for scanning the sample in transmission mode or reflection mode;
   c) illuminating the sample with the light beam and diffracting the light beam according to the actual pattern present on the sample to form a diffracted light beam;
   d) detecting the diffracted light beam in terms of position related intensities with a position sensitive detector;
   e) analyzing detected intensities, and thereby obtaining a diffraction image that is responsive to the actual pattern block on the sample;
   f) repeatedly comparing diffraction images with previously obtained diffraction images thereby determining a trustworthy diffraction image when a first predetermined number of diffraction images out of a second predetermined number of diffraction images are identical, and marking all diffraction images deviating from the trustworthy diffraction image as being related to a pattern block potentially having a defect; and
   g) identifying the position of the pattern block potentially having a defect for further inspection of the position on the sample.

2. The method according to claim 1, wherein the illuminating step comprises illuminating the sample with the light beam at an angle of 0 to 80° relative to a surface normal of the sample.

3. The method according to claim 1, which comprises calculating a predicted diffraction image of the desired pattern block and comparing the trustworthy diffraction image with the predicted diffraction image and, in case of congruency, authorizing for the identification of obtained diffraction images deviating from the trustworthy diffraction image.

4. The method according to claim 3, which comprises calculating the predicted diffraction image using Fourier or Fresnel calculations.

5. The method according to claim 1, wherein the light source is configured to provide radiation selected from the group consisting of visible light, UV light, DUV light, EUV light, soft X-rays, and hard X-rays.

6. The method according to claim 1, wherein the actual pattern block is a structure of an electronic circuitry in a semiconductor chip.

7. The method according to claim 1, wherein the desired pattern block is an engineered pattern block on the sample.

8. The method according to claim 1, which comprises analyzing the detected intensities and reconstructing an aereal image of the sample using iterative reconstruction algorithms.

9. The method according to claim 8, wherein the iterative reconstruction algorithms are a ptychographic algorithm or a priori knowledge of the sample.

10. A system for scanning scattering contrast inspection for identifying defects in an actual pattern of a sample as compared to a desired pattern of the sample, the system comprising:
    a sample holder for holding the sample having the actual pattern, said pattern comprising absorbing and or phase-shifting materials and the sample carrying periodic repetitions of a pattern block;
    a light source for generating a light beam for scanning the sample in transmission mode or reflection mode by illuminating the sample with the light beam;
    a position sensitive detector for detecting a diffracted light beam in terms of position related intensities thereof;
    a computing device connected to said detector, said computing device being configured:
       to process data for analyzing the intensities detected by said detector and to obtain a diffraction image responsive to the actual pattern block on the sample;
       to calculate a predicted diffraction image of the desired pattern;
       to repeatedly compare the diffraction images with previously obtained diffraction images thereby determining a trustworthy diffraction image when a first predetermined number of diffraction images out of a second predetermined number of diffraction images are identical, and to mark all diffraction images deviating from the trustworthy diffraction image as being related to a pattern block potentially comprising a defect; and
       to identify a position of the pattern block potentially comprising a defect for further inspection of the position on the sample.

11. The system according to claim 10, wherein said light source is configured for illuminating the sample with the light beam at an angle of 0 to 80° relative to a surface normal of the sample.

12. The system according to claim 10, wherein said computing device is configured for calculating the predicted diffraction image using Fourier or Fresnel calculations.

13. The system according to claim 10, wherein said computing device is further configured for calculating a predicted diffraction image of the desired pattern block, wherein the trustworthy diffraction image is compared to the predicted diffraction image and, in case of congruency, is authorized for the identification of diffraction images deviating from the trustworthy diffraction image.

14. The system according to claim 10, wherein said light source is configured to provide light radiation selected from the group consisting of visible light, UV light, DUV light, EUV light, soft X-rays, and hard X-rays.

15. The system according to claim 10, wherein the detected intensities are analyzed using a ptychographic algorithm.

16. A method for scanning scattering contrast inspection for identifying defects in an actual pattern block on a sample as compared to a desired pattern block on the sample, the method comprising:
    a) providing the sample with the actual pattern block, the pattern having absorbing and/or phase-shifting materials and the sample carrying periodic repetitions of the pattern block;
    b) providing a defect library with a number of possible defects that may occur for the pattern block and calculating a diffraction image for each possible defect to thereby determine regions of interest in the reconstructed diffraction image which deviate from a reconstructed diffraction image for a defect-free desired pattern block;

c) providing a light source for generating a light beam for scanning the sample in transmission mode or reflection mode;

d) illuminating the sample with the light beam, thereby diffracting the light beam according to the actual pattern present on the sample;

e) detecting the diffracted light beam in terms of position related intensities thereof with a position sensitive detector;

f) analyzing the detected intensities, and thereby obtaining a reconstructed diffraction image responsive to the actual pattern block on the sample and comparing the reconstructed diffraction image only in the predetermined regions of interest thereby identifying pattern blocks potentially comprising a defect; and g) identifying a position of the pattern block that potentially comprises a defect for further inspection of the position thereof on the sample.

17. The method according to claim 16, wherein the illuminating step comprises illuminating the sample with the light beam at an angle of 0 to 45° relative to a surface normal of the sample.

* * * * *